(12) United States Patent
Ma

(10) Patent No.: US 12,150,678 B2
(45) Date of Patent: Nov. 26, 2024

(54) CUSTOMIZED POSTERIOR ATLANTOAXIAL REDUCTION FIXATORWITH SCREWS AND RODS

(71) Applicant: Xiangyang Ma, Guangzhou (CN)

(72) Inventor: Xiangyang Ma, Guangzhou (CN)

(*) Notice: Subject to any disclaimer, the term of this patent is extended or adjusted under 35 U.S.C. 154(b) by 1289 days.

(21) Appl. No.: 16/822,046

(22) Filed: Mar. 18, 2020

(65) Prior Publication Data
US 2021/0290272 A1 Sep. 23, 2021

Related U.S. Application Data

(63) Continuation-in-part of application No. 16/630,479, filed as application No. PCT/CN2016/110718 on Dec. 19, 2016, now abandoned.

(30) Foreign Application Priority Data

| Dec. 23, 2015 | (CN) | 201521079127.3 |
| Dec. 23, 2015 | (CN) | 201521079131.X |
| Jul. 15, 2016 | (CN) | 201610557989.5 |
| Jul. 15, 2016 | (CN) | 201620746909.6 |
| Jul. 18, 2016 | (CN) | 201610560272.6 |
| Jul. 18, 2016 | (CN) | 201620760760.7 |

(51) Int. Cl.
A61B 17/70 (2006.01)

(52) U.S. Cl.
CPC ...... *A61B 17/7032* (2013.01); *A61B 17/7011* (2013.01); *A61B 17/7014* (2013.01)

(58) Field of Classification Search
CPC ............ A61B 17/7041; A61B 17/7043; A61B 17/7049; A61B 17/705; A61B 17/7052; A61B 17/7004; A61B 17/7005; A61B 17/701
See application file for complete search history.

(56) References Cited

U.S. PATENT DOCUMENTS

| 4,815,453 A | * | 3/1989 | Cotrel | A61B 17/7049 606/279 |
| 4,854,304 A | * | 8/1989 | Zielke | A61B 17/7008 606/57 |
| 5,005,562 A | * | 4/1991 | Cotrel | A61B 17/7032 606/330 |
| 5,084,048 A | * | 1/1992 | Jacob | A61B 17/7037 606/264 |

(Continued)

Primary Examiner — Lynnsy M Summitt
(74) Attorney, Agent, or Firm — Bayramoglu Law Offices LLC

(57) ABSTRACT

A customized posterior atlantoaxial reduction fixator with screws and rods, including two supporting-screws, two pulling-screws, two variable cross section fixing rods, a bracing beam, two lock nuts and two pressing rod nuts. Each of the supporting-screws includes a first head and a first body, and each of the pulling-screws includes a second head and a second body; tips of both the first body and the second body are provided with a tapered thread; both the first head and the second head are provided with nail grooves inside, with U-shaped grooves on the sides; each of the a plurality of nail grooves is provided with an internal thread inside; the second head is provided with a long arm nail groove, with an annular recess configured on the middle part of an outer wall.

8 Claims, 7 Drawing Sheets

(56) References Cited

U.S. PATENT DOCUMENTS

| | | | | |
|---|---|---|---|---|
| 5,217,461 A * | 6/1993 | Asher | A61B 17/7041 | 606/261 |
| 5,242,443 A * | 9/1993 | Kambin | A61B 17/7007 | 606/267 |
| 5,242,446 A * | 9/1993 | Steffee | A61B 17/7001 | 606/264 |
| 5,261,907 A * | 11/1993 | Vignaud | A61B 17/7052 | 606/252 |
| 5,403,314 A * | 4/1995 | Currier | A61B 17/7004 | 403/396 |
| 5,486,174 A * | 1/1996 | Fournet-Fayard | A61B 17/7037 | 606/267 |
| 5,545,167 A * | 8/1996 | Lin | A61B 17/7052 | 606/278 |
| 5,593,408 A * | 1/1997 | Gayet | A61B 17/7055 | 606/261 |
| 6,264,658 B1 * | 7/2001 | Lee | A61B 17/7052 | 606/252 |
| 6,379,354 B1 * | 4/2002 | Rogozinski | A61B 17/80 | 606/264 |
| 6,485,491 B1 * | 11/2002 | Farris | A61B 17/7035 | 606/264 |
| 6,641,583 B2 * | 11/2003 | Shluzas | A61B 17/701 | 606/252 |
| 7,291,151 B2 * | 11/2007 | Alvarez | A61B 17/7037 | 606/305 |
| 7,645,294 B2 * | 1/2010 | Kalfas | A61B 17/7049 | 606/267 |
| 7,704,271 B2 * | 4/2010 | Abdou | A61B 17/7046 | 606/264 |
| 7,708,764 B2 * | 5/2010 | Simonson | A61B 17/7041 | 606/279 |
| 7,717,939 B2 * | 5/2010 | Ludwig | A61B 17/7049 | 606/267 |
| 7,722,648 B2 * | 5/2010 | Drewry | A61B 17/7052 | 606/250 |
| 7,837,714 B2 * | 11/2010 | Drewry | A61B 17/7052 | 606/250 |
| 7,909,857 B2 * | 3/2011 | Ogilvie | A61B 17/7005 | 606/279 |
| 7,931,676 B2 * | 4/2011 | Veldman | A61B 17/7008 | 606/261 |
| 7,941,221 B2 * | 5/2011 | Foley | A61N 1/32 | 607/40 |
| 8,137,384 B2 * | 3/2012 | Heiges | A61B 17/864 | 606/254 |
| 8,162,986 B2 * | 4/2012 | Zehnder | A61B 17/705 | 606/260 |
| 8,246,665 B2 * | 8/2012 | Butler | A61B 17/7037 | 606/308 |
| 8,257,397 B2 * | 9/2012 | Winslow | A61B 17/7046 | 606/264 |
| 8,277,489 B2 * | 10/2012 | Saidha | A61B 17/7052 | 606/250 |
| 8,353,937 B2 * | 1/2013 | Capote | A61B 17/705 | 606/272 |
| 8,382,803 B2 * | 2/2013 | Schmocker | A61B 17/7022 | 606/264 |
| 8,414,614 B2 * | 4/2013 | Firkins | A61B 17/701 | 606/246 |
| 8,419,773 B2 * | 4/2013 | Biedermann | A61B 17/705 | 606/259 |
| 8,518,080 B2 * | 8/2013 | Egli | A61B 17/7001 | 606/246 |
| 8,523,911 B2 * | 9/2013 | Jani | A61B 17/7032 | 606/264 |
| 8,641,735 B2 * | 2/2014 | Serbousek | A61B 17/7004 | 606/259 |
| 8,657,856 B2 * | 2/2014 | Gephart | A61B 17/705 | 606/256 |
| 8,663,289 B2 * | 3/2014 | Schwab | A61B 17/7032 | 606/267 |
| 8,672,978 B2 * | 3/2014 | Dant | A61B 17/705 | 606/264 |
| 8,709,049 B2 * | 4/2014 | Klein | A61B 17/7091 | 606/264 |
| 8,858,605 B1 * | 10/2014 | Glatzer | A61B 17/7089 | 606/267 |
| 8,870,922 B2 * | 10/2014 | Hammer | A61B 17/7052 | 606/253 |
| 8,920,475 B1 * | 12/2014 | Ziemek | A61B 17/7052 | 606/267 |
| 8,979,903 B2 * | 3/2015 | Capote | A61B 17/7007 | 606/259 |
| 8,992,576 B2 * | 3/2015 | Keyer | A61B 17/7037 | 606/257 |
| 9,072,546 B2 * | 7/2015 | Trieu | A61B 17/7031 | |
| 9,101,400 B2 * | 8/2015 | Trieu | A61B 17/7026 | |
| 9,232,964 B2 * | 1/2016 | Freudiger | A61B 17/7004 | |
| 9,247,964 B1 * | 2/2016 | Shoshtaev | A61B 17/7083 | |
| 9,387,013 B1 * | 7/2016 | Shoshtaev | A61B 17/7055 | |
| 9,393,048 B2 * | 7/2016 | Carbone | A61B 17/7037 | |
| 9,510,862 B2 * | 12/2016 | Montello | A61B 17/7011 | |
| 9,579,125 B2 * | 2/2017 | Raju | A61B 17/7037 | |
| 9,795,413 B2 * | 10/2017 | Barrus | A61B 17/7025 | |
| 9,895,174 B2 * | 2/2018 | Ozdil | A61B 17/7052 | |
| 10,117,679 B2 * | 11/2018 | Biyani | A61B 17/7032 | |
| 10,463,401 B2 * | 11/2019 | Mire | A61B 17/7032 | |
| 10,485,596 B2 * | 11/2019 | Koller | A61B 17/8605 | |
| 10,517,644 B2 * | 12/2019 | Fessler | A61B 17/8888 | |
| 2005/0059972 A1 * | 3/2005 | Biscup | A61B 17/7061 | 606/907 |
| 2006/0241593 A1 * | 10/2006 | Sherman | A61B 17/7032 | 606/264 |
| 2010/0042154 A1 * | 2/2010 | Biedermann | B26F 1/02 | 83/684 |
| 2010/0114165 A1 * | 5/2010 | Ely | A61B 17/7004 | 606/264 |
| 2010/0114167 A1 * | 5/2010 | Wilcox | A61B 17/705 | 606/264 |
| 2010/0249846 A1 * | 9/2010 | Simonson | A61B 17/8625 | 606/264 |
| 2011/0009906 A1 * | 1/2011 | Hestad | A61B 17/7022 | 606/264 |
| 2011/0029018 A1 * | 2/2011 | Carlos | A61B 17/7014 | 606/279 |
| 2012/0041490 A1 * | 2/2012 | Jacob | A61B 17/7032 | 606/279 |
| 2012/0130436 A1 * | 5/2012 | Haskins | A61B 17/7032 | 606/301 |
| 2012/0215263 A1 * | 8/2012 | Lee | A61B 17/8685 | 606/305 |
| 2012/0253400 A1 * | 10/2012 | Clark | A61B 17/705 | 606/264 |
| 2012/0253401 A1 * | 10/2012 | Clark | A61B 17/7032 | 606/264 |
| 2012/0271353 A1 * | 10/2012 | Barry | A61B 17/705 | 606/265 |
| 2012/0290013 A1 * | 11/2012 | Simonson | A61B 17/7004 | 606/279 |
| 2012/0296380 A1 * | 11/2012 | Simonson | A61B 17/7038 | 606/279 |
| 2013/0030470 A1 * | 1/2013 | Karas | A61B 17/1757 | 606/264 |
| 2013/0345755 A1 * | 12/2013 | Prajapati | A61B 17/7037 | 606/273 |
| 2014/0188178 A1 * | 7/2014 | Juchno | A61B 17/8047 | 606/292 |
| 2014/0228887 A1 * | 8/2014 | Raju | A61B 17/7035 | 606/257 |
| 2016/0128734 A1 * | 5/2016 | Barlett | A61B 17/7052 | 606/264 |
| 2018/0116695 A1 * | 5/2018 | Armstrong | A61B 17/7011 | |
| 2018/0303519 A1 * | 10/2018 | Liu | A61B 17/88 | |
| 2019/0117272 A1 * | 4/2019 | Klausman | A61B 17/7052 | |

(56) References Cited

U.S. PATENT DOCUMENTS

2019/0336178 A1* 11/2019 Finn .................. A61B 17/7052
2019/0374257 A1* 12/2019 Bedor ................ A61B 17/7004
2020/0146728 A1* 5/2020 Daniels .............. A61B 17/7034

* cited by examiner

CUSTOMIZED POSTERIOR ATLANTOAXIAL REDUCTION FIXATOR WITH SCREWS AND RODS

CROSS REFERENCE TO THE RELATED APPLICATIONS

This is a continuation-in-part of the U.S. application Ser. No. 16/630,479, filed on Jan. 13, 2020, which was the National Stage of International Application No. PCT/CN2016/110718, filed on Dec. 19, 2016, which is based upon and claims priority to Chinese Patent Application No. 201521079127.3, filed on Dec. 23, 2015; Chinese Patent Application No. 201521079131.X, filed on Dec. 23, 2015; Chinese Patent Application No. 201610557989.5, filed on Jul. 15, 2016; Chinese Patent Application No. 201610560272.6, filed on Jul. 18, 2016; Chinese Patent Application No. 201620746909.6, filed on Jul. 15, 2016; and Chinese Patent Application No. 201620760760.7, filed on Jul. 18, 2016, the entire contents of which are incorporated herein by reference.

TECHNICAL FIELD

The invention relates to a technical field of medical apparatus and instruments, and more specifically to a customized posterior atlantoaxial reduction fixator with screws and rods.

BACKGROUND

The posterior atlantoaxial transarticular screw (Magerl screw) fixation technique has been successfully developed since 1979, it was always considered as the golden standard of a surgery of atlantoaxial fixation. However, with the advent of the posterior atlantal lateral mass screw technique (Goel-Harms technique), the posterior short-segment screws and rods fixation technique composed of atlas screw combined with axis screw gradually replaces Magerl screw, and becomes a preferred method for the posterior atlantoaxial fixation, regarded as the new golden standard of the surgery. The posterior short-segment screws and rods fixation technique separately arranges screws in the atlas and the axis, it not only has advantages including small entry angle of screw, wide range of application and high fixation strength, but also can play a role in spondylolisthesis reduction during operation, so as to dramatically improve the effectiveness, safety, applicability and convenience of the treatment of atlantoaxial dislocation.

However, fixators with screws and rods currently used for atlantoaxial dislocation are not customized designed for the atlantoaxial dislocation, they are just general fixators for posterior cervical vertebra, and a variety of defects of them have been observed in an operation process of the clinic treatment of the atlantoaxial dislocation. Therefore, it is necessary to further develop and improve related technologies, such as the improvement of the existing fixators with screws and rods.

A universal screws and rods system for posterior cervical vertebra usually comprises screws for screwing into vertebral bodies, cylindrical fixing rods for connecting the screws in different vertebral bodies, lateral combination parts configured on two fixing rods and so on. In clinical practice, the fixing rods need to be pre-bent frequently based on physiological curvature of the spine itself or requirement of reduction for dislocation, but the fixing rods are cylindrical, so they tend to rotate within the screw slots. Especially, during a surgery for atlantoaxial dislocation, due to small space for the atlas and the axis, it is difficult to use auxiliary tools such as rotary rods and adjusting rod. Additionally, nonosseous tissues between the atlas and the axis cover the spinal cord, repeated adjustment of the direction of the fixing rods may lead to spinal cord injury caused by misoperation of the auxiliary tools. On the contrary, the present invention provides automatic anti-rotation fixing rods, which could reduce the difficulty of surgery and increase the safety of operation.

Although screws and rods fixation have the function of spondylolisthesis reduction to some extent, when the atlas and the axis are in serious dislocation, the degree of bending of fixing rods should be increased, so as to improve the function of spondylolisthesis reduction. However, the greater the degree of bending of fixing rods is, the more difficult the direction of the fixing rods is maintained, so the operation is more difficult, and the misoperation is likely to occur to cause spinal cord injury. In this invention, the thickness of the bottoms of the screw slots is increased, specialized supporting-screws are designed, not to mention a polyaxial screw and a single-axial screw, with various specifications whose bottom groove are raised 2 mm-6 mm, so that the posterior atlantoaxial reduction fixator can increase lifting distance for improving the function of spondylolisthesis reduction of a screw-rod system, and lower the risk of operation, without adjusting other structures.

When the dislocation of the atlas and the axis occurs, the atlas slides forward, so that the screw slots of the atlas screw and the axis screw are not in the same coronal plane, thus a doctor has to utilize the screw-rod lifting to implement the reduction. However, the existing screws for cervical posterior instrument are polyaxial screws with short arm screw slots, thus configuration and operation of rods are very difficult, especially for the clinical cases in serious dislocation of the atlas and the axis, a doctor always needs to carry out auxiliary operation including lifting the screw and pressing the rod in a narrow space, so as to press the fixing rod into the screw slot of the atlas screw. For this purpose, the present invention designs long arm polyaxial pulling-screw for the atlas, wherein the fixing rod can be imbedded into an extended screw slot directly, and a doctor can gradually tighten a nut to complete the spondylolisthesis reduction of the atlas and the lock of the fixing rod, thus simplifying the arrangement of the rod and the operation of reduction.

Furthermore, for the stability of fixing rods in a surgery, transverse connection is often implemented between two fixing rods, and the traditional transverse connection is lateral combination on fixing rods. Due to short distance between the atlas screw and the axis screw, and the pre-bend of the fixing rod, it is difficult to install the lateral combination on fixing rods, meanwhile, occupying the bone grafting space which is small and which is located between the atlas and the axis. As a result, the applicant designs and provides a bracing beam configured on the head of the screw slot, wherein it is easy to be installed and does not occupy the bone grafting space.

SUMMARY

For solving the abovementioned problems, the present invention provides a customized posterior atlantoaxial reduction fixator with screws and rods. The customized posterior atlantoaxial reduction fixator increases the range of application and implements adjustments according to characteristics of the dislocation of the atlas and the axis, so as to adapt to the operation of reduction for the dislocation of the atlas and the axis, improving the function of reduction, simplifying surgical procedures and increasing safety.

The customized posterior atlantoaxial reduction fixator with screws and rods comprises two supporting-screws, two pulling-screws, two variable cross section fixing rods, a bracing beam, two lock nuts and two pressing rod nuts. each of the variable cross section fixing rods is configured to connect a supporting-screw and a pulling-screw, the bracing beam is configured to connect the supporting-screws on the variable cross section fixing rods; wherein each of the supporting-screws comprises a first head (namely the head of the supporting-screw) and a first body (namely the body of the supporting-screw), and each of the pulling-screws comprises a second head (namely the head of the pulling-screw) and a second body (namely the body of the pulling-screw); both the first head and the second head are provided with nail grooves, with U-shaped grooves on the sides; wherein each of the nail grooves is provided with internal thread inside, so that the lock nut can be connected to the internal thread of the nail groove of the first head, and the pressing rod nut can be connected to the internal thread of the nail groove of the second head; each of the variable cross section fixing rods passes through the U-shaped grooves and is fastened by the lock nut; the bottoms of the nail grooves of the supporting-screws are 2-6 mm higher than the bottoms of the nail grooves of the pulling-screws. In traditional structure, the height of the bottom of the nail groove of a supporting-screw is the same as that of the bottom of the nail groove of a pulling-screw; the design according to the present application result in a higher bottom of the nail groove of the supporting-screw, 2-6 mm higher than traditional height. When a patient is in serious dislocation, the height of the bottom of the traditional nail groove would lead to a short distance for spondylolisthesis reduction, if we need to pull a greater distance, much degree of bend of the fixing rod will be required to improve the effect of spondylolisthesis reduction. However, the greater the degree of bending of fixing rods is, the more difficult the direction of the fixing rods is maintained, so the operation is more difficult, and the misoperation is likely to occur to cause spinal cord injury. In this invention, the thickness of the bottoms of the screw slots is increased, specialized supporting-screws are designed, with various specifications whose bottom groove are raised 2 mm-6 mm, so that the posterior atlantoaxial reduction fixator can increase lifting distance for improving the function of spondylolisthesis reduction of a screw-rod system, and lower the risk of operation, without adjusting other structures. Furthermore, each of the variable cross section fixing rods is provided with an anti-rotation joint portion matched with the U-shaped grooves; the anti-rotation joint portion is located on one end of the universal round bar of the variable cross section fixing rod; the cross section of the anti-rotation joint portion includes a curved part and a rectangular part; wherein the curved part is a semicircle, with a radius being equal to that of the round bar; wherein the length of a long side of the rectangular part is the same as the diameter of the curved part, and the length of a short side of the rectangular part is the same as the radius of the round bar.

Since the radius of the curved part is equal to that of the round bar, which means that this part does not increase, and the length of a long side of the rectangular part is the same as the diameter of the round bar, and the length of a short side of the rectangular part is the same as the radius of the round bar, the distance from the top surface of the rectangular part to the bottom of the curved part is just the same as the diameter of the round bar. As a result, when the anti-rotation joint portion is placed in the U-shaped groove of the screw, it does not increase the overall height, consistent with the height of the round bar. As you see, this delicate design shows nice technical rationality, it can effectively improve suitability of a tool and a screw, and reduce the difficulty of operation. Specifically, this delicate design effectively avoid the problems of stress concentration, needs of adjustment of sizes of tools (such as a screw driver, a wrench, a rod bending tool), and needs of deepening the U-shaped groove of the screw or decreasing the thickness of the nut probably caused by change in height, diameter, thickness and so on. As we know, traditional shapes such as oval, can also play a role in anti-rotation, but if the specification of a product is changed (for example, the diameter), other tools may no longer match, in this case, we have to additionally produce customized tools, including a screw driver, a wrench and a rod bending tool, so the production cost will rise remarkably, and they will be not convenient to use.

The present invention has improved the fixing rod, taking effect and performance in practice into full consideration. The cross section of the round bar is composed of two semicircles which are vertically symmetrical, wherein one semicircle is corresponding to the curved part, and the other semicircle is corresponding to the rectangular part, whose long side is equal to the diameter and whose short side is equal to the radius.

As a preferred embodiment of the present invention, both ends of the anti-rotation joint portion are about 2-3 mm longer than both ends of the U-shaped groove respectively. The variable cross section fixing rod according to the present application consists of a universal round bar and an anti-rotation joint portion, wherein both ends of the anti-rotation joint portion are about 2-3 mm longer than both ends of the U-shaped groove respectively, wherein the length of the round bar is relatively long, so the round bar could be cut out by a specialized cutting rod tool based on the amount of segments fixed in the spine during a surgery. Moreover, the variable cross section fixing rod according to the present application only has one anti-rotation joint portion at one end, because just one screw nut is required to fasten the variable cross section fixing rod through the anti-rotation joint portion, so that the direction of the whole variable cross section fixing rod has been determined; the other part of the variable cross section fixing rod is designed as a non-anti-rotation portion, which is a round bar, convenient for the variable cross section fixing rods matching with U-shaped grooves of other vertebral screws. The delicate design makes possible the automatic anti-rotation of the variable cross section fixing rod, and can avoid application of auxiliary tools such as a rotary bar, so the variable cross section fixing rod can not only precisely preset its direction, reduce the difficulty of operation in a surgery, but also be suitable for existing screw systems and accompanying tools, with excellent compatibility.

As a preferred embodiment of the present invention, the second head is provided with a long arm nail groove, with an annular recess configured on the middle part of the outer wall. The traditional structure is a short arm nail groove. In clinical practice, if the dislocation of the atlas and the axis occurs, the atlas will slide forward, so that the screw slots of the atlas screw and the axis screw will not be in the same coronal plane, thus a doctor has to utilize the screw-rod lifting to implement the reduction. However, the existing screws for cervical posterior instrument are polyaxial screws with short arm screw slots, thus configuration and operation of rods are very difficult, especially for the clinical cases in serious dislocation of the atlas and the axis, a doctor always needs to carry out auxiliary operation including lifting the screw and pressing the rod in a narrow space. For overcoming the defect, the applicant has designed a lifting polyaxial screw with long arm for atlas, a doctor can gradually tighten a nut to complete the spondylolisthesis reduction of the atlas and the lock of the fixing rod, thus simplifying the arrangement of the rod and the operation of reduction. Since the second head is separated into upper and lower portions through the annular recess, after the reduction, the upper portion could be broken off at the annular recess; accordingly, this kind of long arm structure expands the scope of application, and improves practicality and convenience.

More preferably, the second head is separated into upper and lower portions through the annular recess, wherein the height ratio of the upper portion to the lower portion is N/1, wherein $N \geq 1$. In fact, 1 height unit (N=1) means the locking depth where a traditional pressing rod nut is used to fasten the fixing rod, in this case, the lower edge of the annular recess aligns to a top surface where the pressing rod nut is tightened and locked with the second head, after locking, it could be broken off through the annular recess. Since different patients may suffer different levels of atlantoaxial dislocation, pulling-screws with N=1 are suitable for slight dislocation. However, with respect to serious dislocation, the traditional pulling-screws with N=1 cannot satisfy normal reduction operation any more, because the distance between a fixing rod and the head of a pulling-screw is still too long, and medical staff have to take advantage of a pressing rod device to press the fixing rod into the head of a pulling-screw, with quite difficult operation. In contrast, as described in the present application, medical staff could utilize the second head with N=2 or N=3, so as to significantly increase the height of the second head, so that the fixing rod can fall into the U-shaped groove of the second head, thus the reduction and the fixation can be achieved by tightening the pressing rod nut. As you see, this structure may provide medical staff with more options, it also extends the scope of application of the product in dislocation at the same time.

As a preferred embodiment of the present invention, the pulling-screw is a polyaxial screw, with the second head connected to the second body which has a tapered thread tip. As we know, the preparation of the screw path of atlantoaxial pedicle and the screwing of screws are so difficult, especially, if the height of the posterior arch of atlas at the screw entering point is too small, even though an operator (e.g. a doctor) succeeds in the preparation of the screw path, the tapping process of a tapered thread tip or the screwing process of a screw can easily lead to bone fracture at the inferior wall of the posterior arch of atlas, resulting in the slide-out of a screw tap or a screw, difficult to access to the previous correct screw path. In this case, repeated adjustments are inevitable during a surgery, for the purpose of accurately screwing the screws, but repeated adjustments are not only time-consuming and arduous, but also take a risk of venous plexus and spinal cord injury. Therefore, the applicant designs the thread of the body part as a tapered thread, wherein the diameter of the front end of the screw becomes smaller, so as to automatically enter the correct screw path, thus increasing the convenience and safety of a surgery.

As a preferred embodiment of the present invention, the first body of the supporting-screw is a single-axial screw which is fastened to the first head, having a tapered thread tip; or the first body of the supporting-screw is a polyaxial screw which is fastened to the first head, having a tapered thread tip. As a result, a single-axial screw or a polyaxial screw could be selected according to different usage requirements.

As a further preferred embodiment of the present invention, both sides of the bracing beam are provided with transverse openings, each of which is an approximative rectangle, with two curved short sides; this kind of design makes the bracing beam has a greater and adjustable connection distance. One end of the lock nut is connected to the first head through thread, the other end of the lock nut is fastened by a screw cap after the other end passes through one of the transverse openings; this kind of design makes the bracing beam to be directly fixed to the supporting-screw, instead of a traditional transverse connection on fixing rods, so it is easy to be placed and arranged, its fixation is not affected by bent rods, more convenient to operate and implement, without occupying the bone grafting space among atlantoaxial spines as well.

As a more preferred embodiment of the present invention, a ring slider is clamped on each of the transverse openings, the inner wall of the transverse opening is provided with a sliding slot, the external wall of the ring slider is provided with a projecting part configured to insert into the sliding slot; wherein the ring slider is provided with a gap, one end of the lock nut passes through the ring slider. For obtaining a greater connection distance between fixing rods and adjustable flexibility, the transverse opening is an approximative rectangle with two curved short sides; for improving the stability of fixation, a ring slider is provided, wherein the ring slider can slide left and right on the transverse opening, and further can be tightly connected with the lock nut, increasing the stability of the connection. Furthermore, the gap of each ring slider is configured for being squeezed so that the ring slider can be clipped into the transverse opening, convenient for manufacture.

More preferably, the external wall of the lock nut comprises a head thread connected with the first head and a screw cap thread connected with the screw cap; the diameter of the head thread is greater than that of the screw cap thread, and is also greater than that of the ring slider; the diameter of the screw cap thread is less than that of the ring slider, the diameter of the external wall of the screw cap is greater than that of the ring slider; a through-hole with hexagonal cross section is configured in the center of the lock nut. As described above, the delimitation of diameter size ensures that both the head thread part and the screw cap part cannot pass through the ring slider, so that the bracing beam is fastened between the screw cap and the head thread, which is specifically the screw cap thread of the lock nut.

As a further preferred embodiment of the present invention, the bracing beam is a straight plate or a curved plate, depending on various situations.

Compared with the existing and general fixators for posterior cervical vertebra in atlantoaxial dislocation, the beneficial effects of the customized posterior atlantoaxial reduction fixator with screws and rods according to the present invention include:

(1) the design of supporting-screws for the axis significantly improves the function of spondylolisthesis reduction; (2) the design of pulling-screws for the atlas makes the arrangement of the rod and the operation of reduction easier, safer and more convenient; (3) the design of the variable cross section fixing rod makes possible the automatic anti-rotation thereof, and the variable cross section fixing rod shows excellent compatibility, with convenient and safe operation; (4) the design of the bracing beam results in simple and reliable connection, without occupying the bone grafting space; (5) the design of tapered thread of a screw tip renders the screwing of a screw accurate, easy, and safe. In conclusion, the customized posterior atlantoaxial reduction fixator with screws and rods according to the present invention thoroughly overcomes the deficiencies including that: traditional fixing rods tend to rotate, traditional screws tend to deviate from the correct screw path, short arm screws lead to difficulty of configuration of fixing rods and reduction. Consequently, the customized posterior atlantoaxial reduction fixator not only increases the safety of a surgery and convenience of the operation, but also dramatically improves the function of spondylolisthesis reduction through the design of the supporting-screw for axis with higher nail groove. Additionally, the implementation of the present invention is not only available in the atlantoaxial, but also available in the whole spine.

BRIEF DESCRIPTION OF THE DRAWINGS

The present invention will be further described below with reference to the accompanying drawings.

DETAILED DESCRIPTION OF THE EMBODIMENTS

Figure 1:
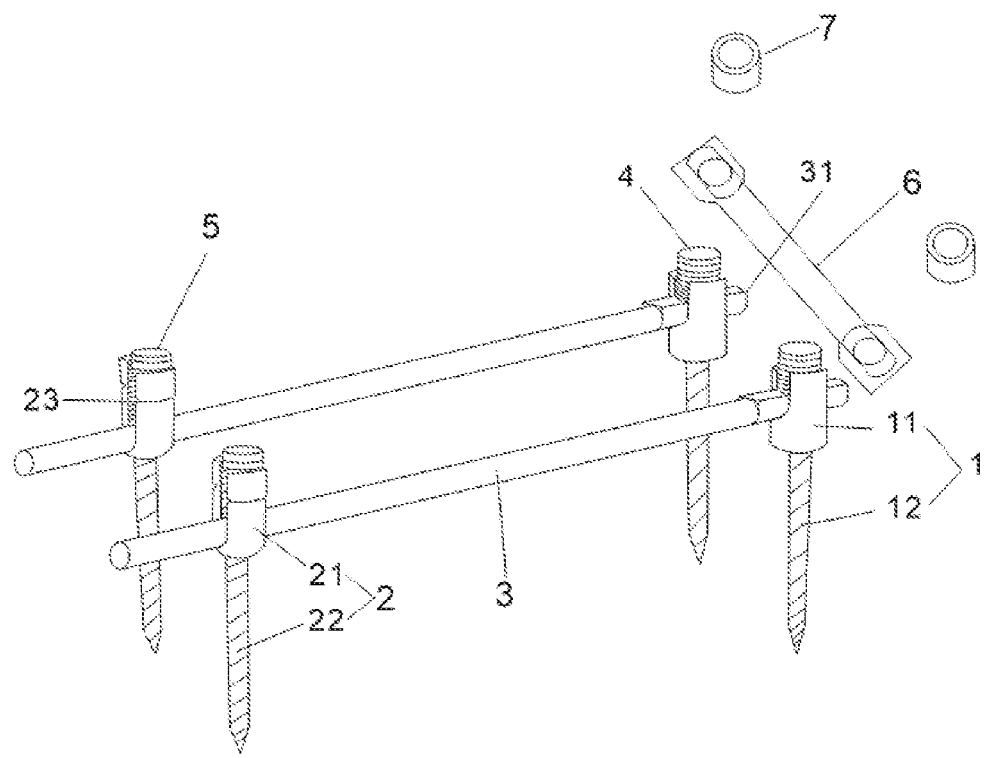
FIG. 1 shows a schematic diagram of the integral structure of the customized posterior atlantoaxial reduction fixator with screws and rods according to the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, certain exemplary embodiments according to the present disclosure will be described with reference to the accompanying drawings.

Figure 2:
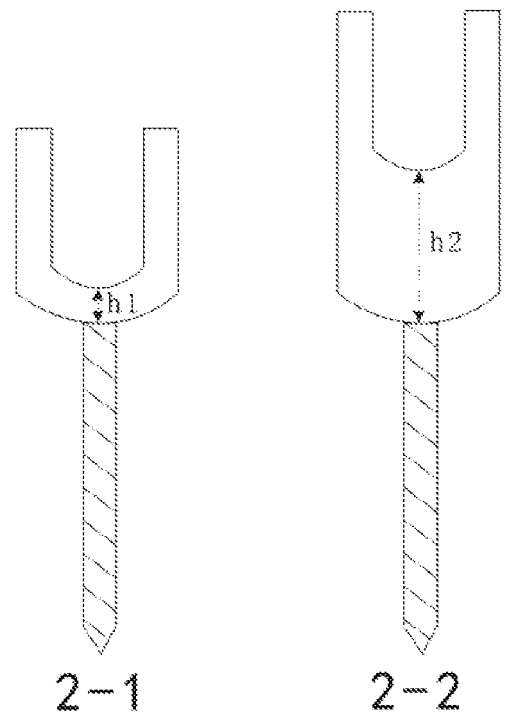
FIG. 2 shows a schematic diagram of the structure of a traditional screw and a supporting-screw according to the present invention; wherein 2-1 represents the traditional screw, and 2-2 represents the supporting-screw.
Figure 9:
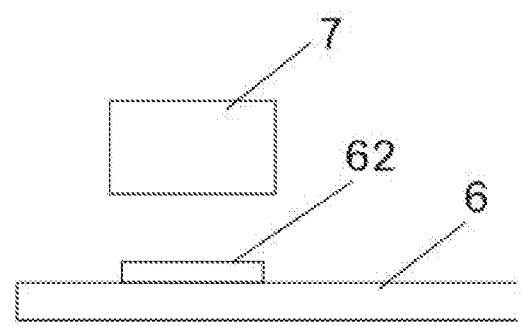
FIG. 9 shows a connection relationship diagram of a lock nut, a bracing beam and a screw cap according to the present invention.
Figure 9:
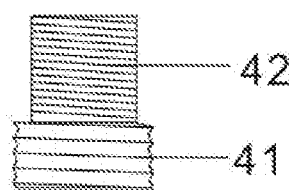
Figure 10:
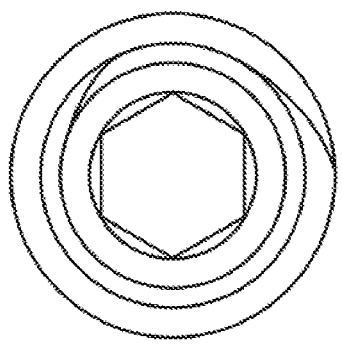
FIG. 10 shows a top view of a lock nut according to the present invention.
Figure 11:
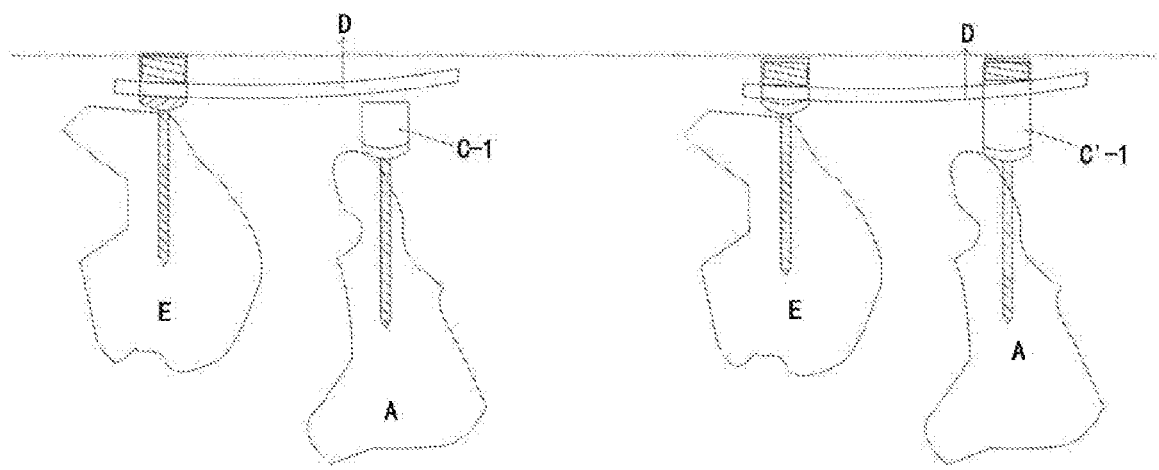
FIG. 11 shows a view of reduction effects with different pulling-screws, wherein the left image shows a traditional pulling-screw with a short arm, which needs pressing rod treatment in use; wherein the right image shows a pulling-screw with a long arm according to the present invention, without the need of pressing rod treatment in use; wherein D represents the direction of lifting, C-1 represents a short arm, C'-1 represents a long arm, E represents a normal axis, and A represents an atlas in dislocation.

As shown in FIGS. 1-12, a customized posterior atlantoaxial reduction fixator with screws and rods, comprising two supporting-screws 1, two pulling-screws 2, two variable cross section fixing rods 3, two lock nuts 4, two pressing rod nuts 5 and a bracing beam 6. Each of the variable cross section fixing rods 3 is configured to connect a supporting-screw 1 and a pulling-screw 2, the bracing beam 6 is configured to connect the supporting-screws 1 on the variable cross section fixing rods 3. Each of the supporting-screws 1 comprises a first head 11 and a first body 12, and each of the pulling-screws 2 comprises a second head 21 and a second body 22; both the first head 11 and the second head 21 are provided with nail grooves, with U-shaped grooves on the sides; wherein each of the nail grooves is provided with internal thread inside, so that the lock nut 4 can be connected to the internal thread of the nail groove of the first head 11, and the pressing rod nut 5 can be connected to the internal thread of the nail groove of the second head 21. Each of the variable cross section fixing rods 3 passes through the U-shaped grooves and is fastened by the lock nut 4 and the pressing rod nut 5. The bottoms of the nail grooves of the supporting-screws 1 are 2-6 mm higher than the bottoms of the nail grooves of the pulling-screws. As shown in FIG. 2, h represents the height of the bottom of the nail groove. Specifically, 2-1 represents the traditional screw with a height h1, and 2-2 represents the supporting-screw with a height h2, wherein the specific value of h2 could be selected in accordance with different situations. In the production of the products, the specific value of h2 could be multiples of 1 mm, and the abovementioned height adjustment can obtain the effect of lifting height of supporting-screws, thus improving the capacity of spondylolisthesis reduction of a screw-rod system. As shown in FIG. 11, the view shows the reduction effects comparison, we can see that a spondylolisthesis reduction system with the pulling-screws with long arms according to the present invention possesses much better effects of spondylolisthesis reduction than a spondylolisthesis reduction system with traditional pulling-screws with short arms.

Figure 5:
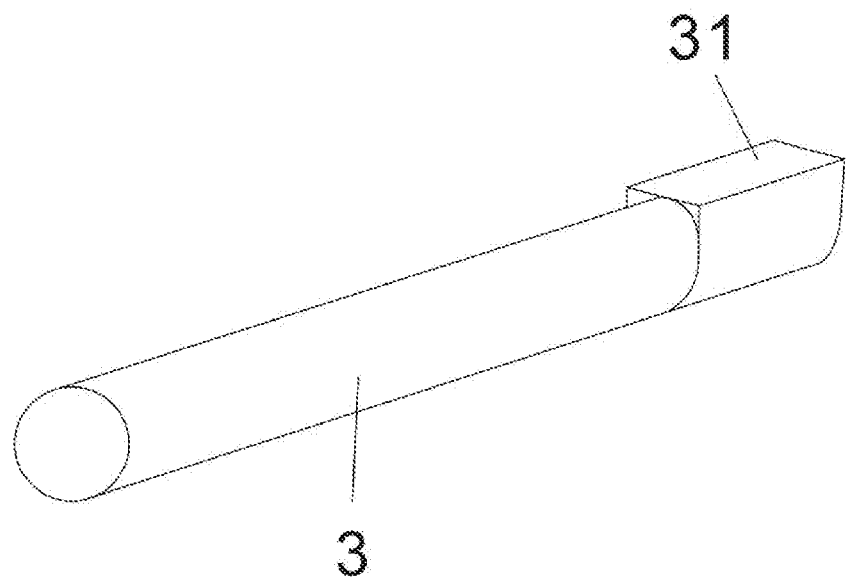
FIG. 5 shows a structural schematic diagram of a variable cross section fixing rod according to the present invention.
Figure 6:
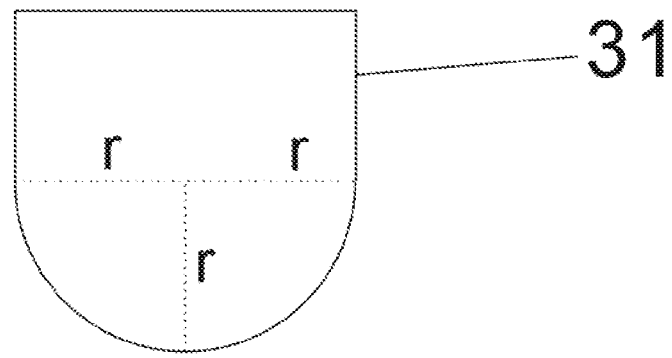
FIG. 6 shows a cross-section view of an anti-rotation joint portion of a variable cross section fixing rod according to the present invention.

Preferably, as shown in FIG. 5, each of the variable cross section fixing rods 3 is provided with an anti-rotation joint portion 31 matched with the U-shaped grooves. The anti-rotation joint portion 31 is located on one end of the universal round bar of the variable cross section fixing rod 3. The cross section of the anti-rotation joint portion 31 includes a curved part and a rectangular part (see FIG. 6); wherein the curved part is a semicircle, with a radius being equal to that of the round bar; wherein the length of a long side of the rectangular part is the same as the diameter of the curved part, and the length of a short side of the rectangular part is the same as the radius of the round bar. Compared to a routine fixing rod without any anti-rotation portion, the anti-rotation joint portion 31 can achieve good effects of anti-rotation. Additionally, unlike an oval anti-rotation structure, there is no need to modify the structure of a screw, there is no need to adjust accompanying tools (e.g. a rod bending tool). Furthermore, the oval anti-rotation fixing rod is less compatible with existing screws and accompanying tools, wherein it needs screws with deeper U-shaped groove. In contrast, the variable cross section fixing rod 3 according to the present invention has both excellent effects of anti-rotation and good compatibility.

Figure 3:
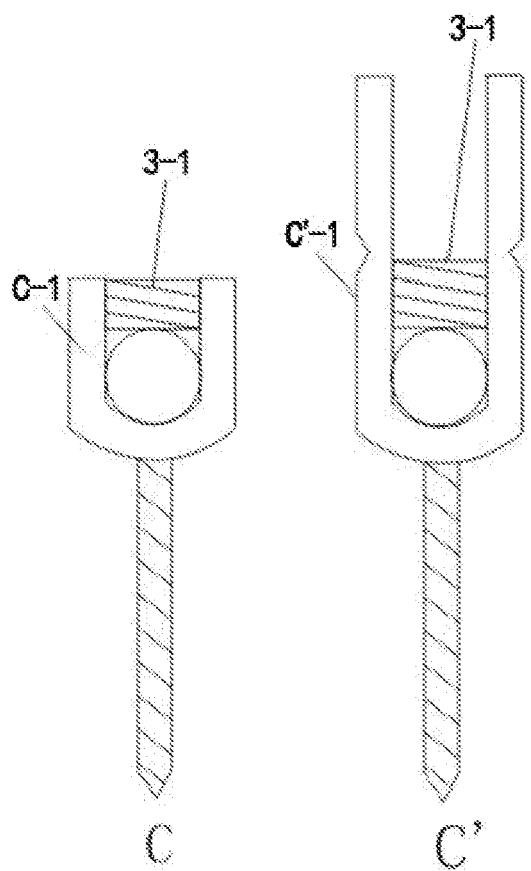
FIG. 3 shows a schematic diagram of the structure of a traditional pulling-screw and a pulling-screw according to the present invention; wherein C' represents the pulling-screw, and C represents the traditional pulling-screw; wherein 3-1 represents a nut, C-1 represents a short arm, and C'-1 represents a long arm.

Preferably, as shown in FIG. 3, the second head 21 is provided with a long arm nail groove, with an annular recess 23 configured on the middle part of the outer wall. When a fixing rod is placed into the long arm nail groove, a doctor can tighten the nut directly, without a pressing rod device or a lifting the screw and pressing the rod device.

Figure 12:
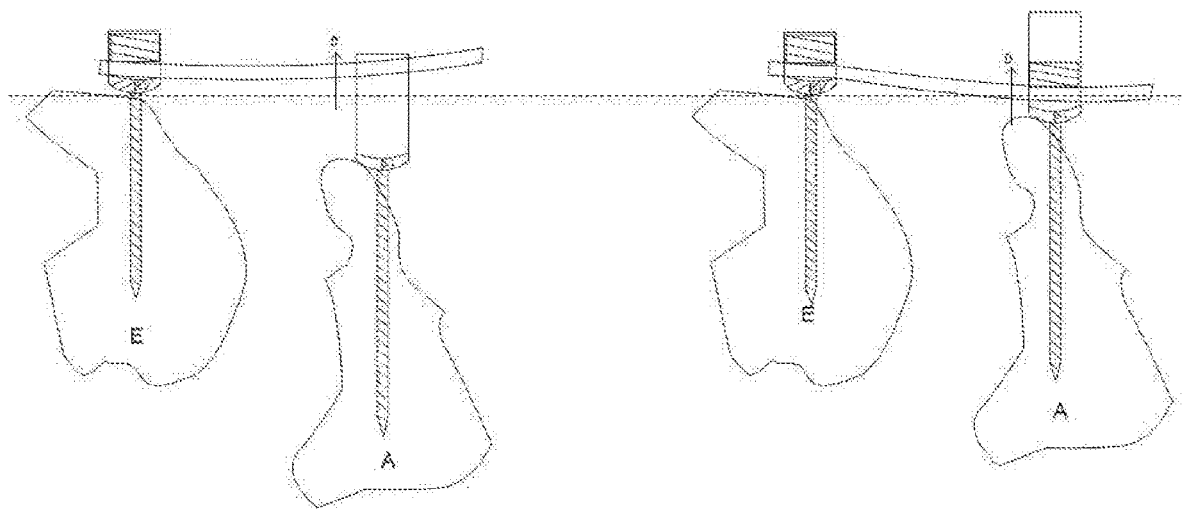
FIG. 12 shows a view of effects before and after reduction with traditional supporting-screws; in the case of serious dislocation, limited height of reduction leads to undesired effects after reduction; wherein D represents the direction of lifting, E represents a normal axis, and A represents an atlas in dislocation.
Figure 13:
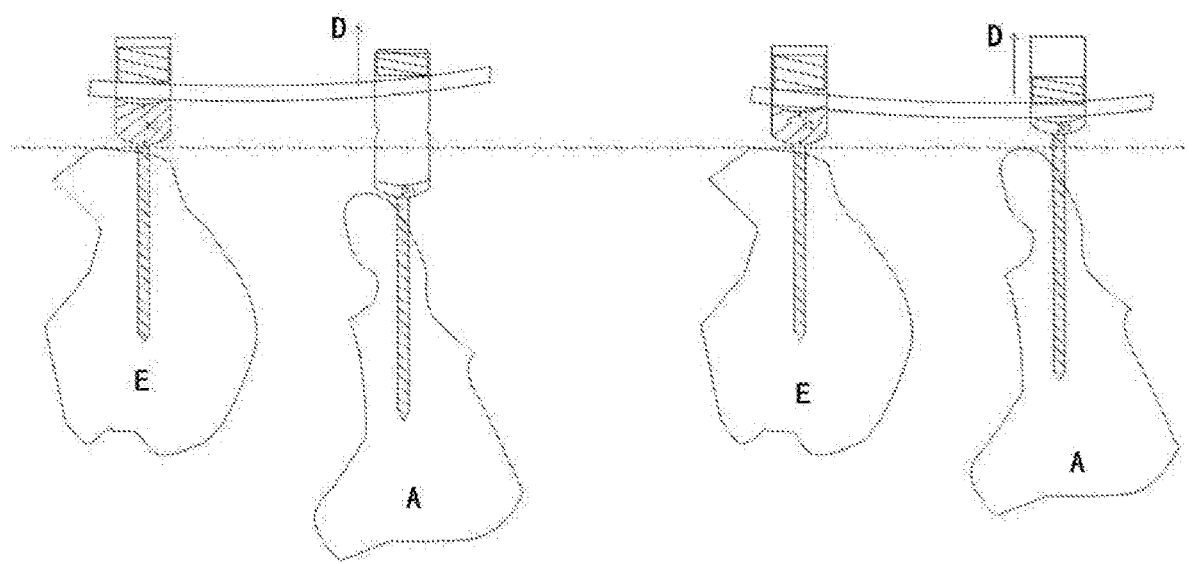
FIG. 13 shows a view of effects before and after reduction with the supporting-screws according to the present invention; wherein the supporting-screws with height-increased nail groove result in desired effects after reduction, with greater lifting height; wherein D represents the direction of lifting, E represents a normal axis, and A represents an atlas in dislocation.

Accordingly, compared to short arm screw, the long arm nail groove is easy to be applied in reduction operation, without pressing the rod, and the needless upper portion can be broken off at the annular recess 23 after the completion of reduction (see FIG. 12).

Figure 4:
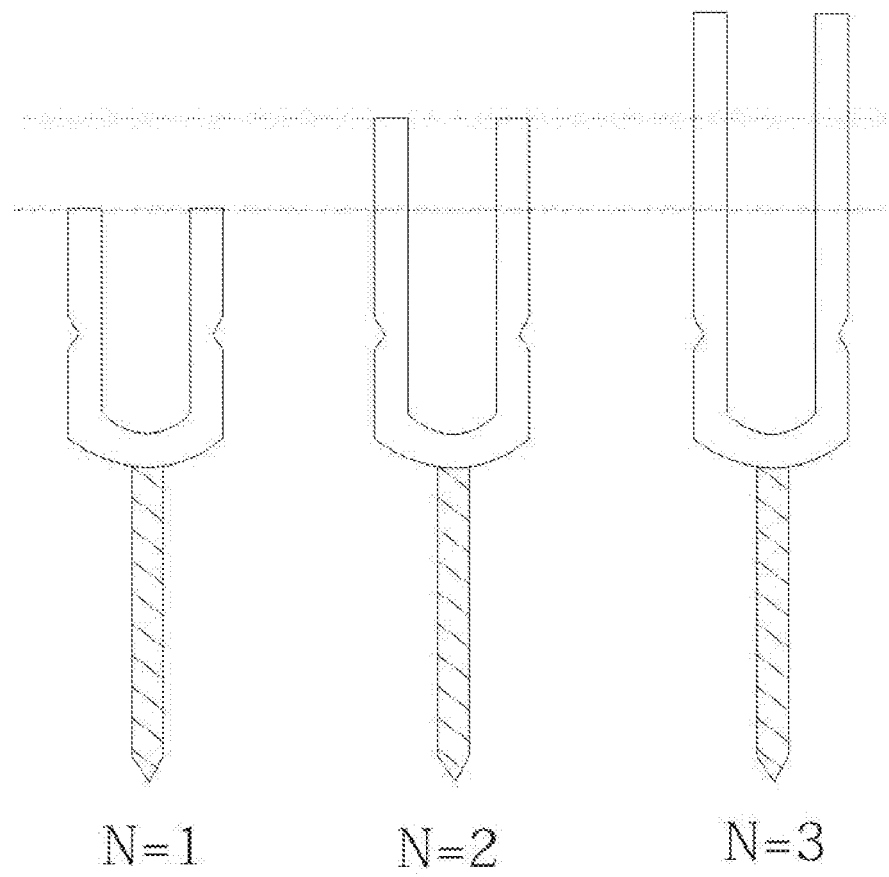
FIG. 4 shows a schematic diagram of the pulling-screws according to the present invention, it shows the second head with different specifications.

More preferably, the second head 21 is separated into upper and lower portions through the annular recess 23, the height ratio of the upper portion to the lower portion is Nil, wherein N≥1. FIG. 4 shows a schematic diagram of the pulling-screws with N=1, 2 and 3.

Preferably, the pulling-screw is a polyaxial screw, with the second head 21 connected to the second body 22 which has a tapered thread tip. The first body 12 of the supporting-screw 1 is a single-axial screw which is fastened to the first head 11, having a tapered thread tip or a polyaxial screw which is fastened to the first head 11, having a tapered thread tip. It is noted that the connection fashion of a polyaxial screw could be as follows: to drill a hole at the bottom of the nail groove of the first head 11 or the second head 21, and let the polyaxial screw pass through the hole.

Figure 7:
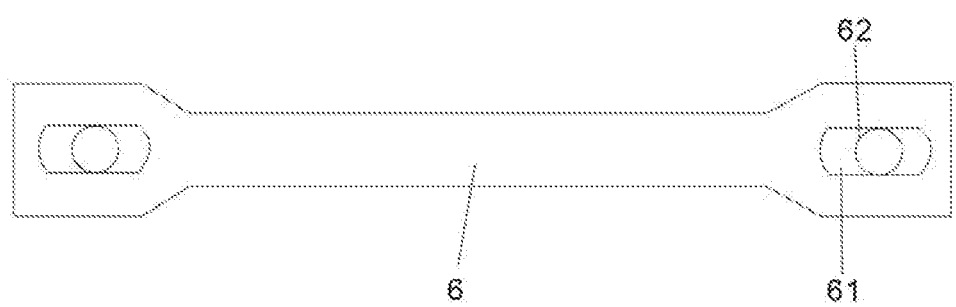
FIG. 7 shows a front view of a bracing beam according to the present invention.
Figure 8:
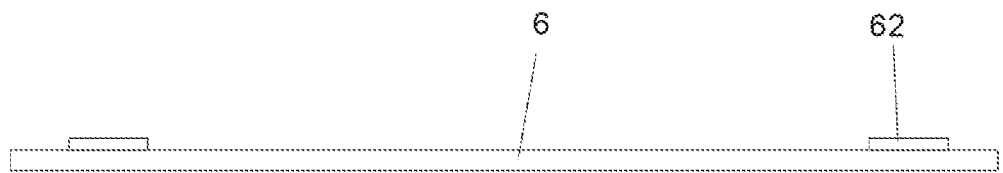
FIG. 8 shows a side view of a bracing beam according to the present invention.

As shown in FIGS. 7 and 8, both sides of the bracing beam 6 are provided with transverse openings 61, each of which is an approximative rectangle, with two curved short sides. One end of the lock nut 4 is connected to the first head 11 through thread, the other end of the lock nut 4 is fastened by a screw cap 7 after the other end passes through one of the transverse openings 61. A ring slider 62 is clamped on each of the transverse openings 61, the inner wall of the transverse opening 61 is provided with a sliding slot, the external wall of the ring slider 62 is provided with a projecting part configured to insert into the sliding slot; wherein the ring slider 62 is provided with a gap, one end of the lock nut 4 passes through the ring slider 62.

As shown in FIGS. 9 and 10, the external wall of the lock nut 4 comprises a head thread 41 connected with the first head 11 and a screw cap thread 42 connected with the screw cap 7. The diameter of the head thread 41 is greater than that of the screw cap thread 42, and is also greater than that of the ring slider 62; the diameter of the screw cap thread 42 is less than that of the ring slider 62, the diameter of the external wall of the screw cap 7 is greater than that of the ring slider 62. Moreover, a through-hole with hexagonal cross section is configured in the center of the lock nut 4.

Preferably, the bracing beam 6 could be a straight plate or a curved plate, depending on various situations.

The following description is intended to illustrate the use procedure of the customized posterior atlantoaxial reduction fixator according to the present invention. In use, firstly, the supporting-screws 1 with higher nail grooves are screwed into a normal axis in accordance with the degree of dislocation, the pulling-screws 2 are screwed into an atlas in dislocation; after that, an anti-rotation joint portion 31 of each of the variable cross section fixing rods 3 is placed into a U-shaped groove of the first head 11, the other end passes through a U-shaped groove of the second head 21, then a lock nut 4 is fastened to the first head 11 through a head thread 41, so that the variable cross section fixing rod 3 is fastened, avoiding rotation. Secondly, a tool is utilized to screw the pressing rod nut 5 into the U-shaped groove of the second head 21, and the variable cross section fixing rod 3 is gradually pressed down to the bottom of the second head 21 during the screwing process; simultaneously, under the lifting force of the variable cross section fixing rod 3, the vertebral body in dislocation gradually restores the normal position, after the completion of screwing, the upper portion of the second head 21 is broken off at the annular recess 23. Thirdly, a ring slider 62 of the bracing beam 6 passes through the screw cap thread 42 of a lock nut 4 on the supporting-screw 1. Finally, the other end of the lock nut 4 is fastened by a screw cap 7, and the process of reduction and fixation is completed.

The above descriptions are only the preferred embodiments of the invention, not thus limiting the embodiments and scope of the invention. Those skilled in the art should be able to realize that the schemes obtained from the contents of the specification and drawings of the invention are within the scope of the invention.

What is claimed is:

1. A customized posterior atlantoaxial reduction fixator comprising:
   two supporting-screws,
   two pulling-screws,
   two variable cross section fixing rods,
   a bracing beam, and
   two lock nuts and two pressing rod nuts;

wherein each of the two variable cross section fixing rods is configured to connect one of the two supporting-screws and one of the two pulling-screws; the bracing beam is configured to connect the two supporting-screws on the two variable cross section fixing rods;

wherein each of the two supporting-screws comprises a first head and a first body, and each of the two pulling-screws comprises a second head and a second body; each of the two first heads and the two second heads is provided with a nail groove, and a U-shaped groove on sides;

wherein each of the nail grooves is provided with an internal thread inside, so that the two lock nuts are connected to the internal threads of the two first heads, respectively, and the two pressing rod nuts are connected to the internal threads of the two second heads, respectively; each of the variable cross section fixing rods passes through the U-shaped grooves of a corresponding supporting screw and pulling screw pair and is fastened by one of the two lock nuts and one of the two pressing rod nuts; bottoms of the nail grooves of the supporting-screws are 2-6 mm higher than bottoms of the nail grooves of the pulling-screws;

wherein each of the variable cross section fixing rods is provided with an anti-rotation joint portion matched with one of the U-shaped grooves of the two first heads, respectively; each of the anti-rotation joint portions is located on one end of a universal round bar of each of the variable cross section fixing rods; a cross section of each of the anti-rotation joint portions includes a curved part and a rectangular part; wherein the curved part is a semicircle, with a radius being equal to that of the round bar; wherein a length of a long side of the rectangular part is equal to a diameter of the curved part, and a length of a short side of the rectangular part is equal to a radius of the round bar;

wherein both sides of the bracing beam are provided with a plurality of transverse openings, each of the plurality of transverse openings is an approximative rectangle, with two curved short sides; one end of each of the two lock nuts is connected to one of the two first heads through a head thread respectively, an other end of the each of the two lock nuts is fastened by a respective screw cap after the other end passes through one of the plurality of transverse openings; and wherein a ring slider is clamped on each of the plurality of transverse openings, an inner wall of each of the plurality of transverse openings is provided with a sliding slot, an external wall of each of the ring sliders is provided with a projecting part configured to be inserted into one of the sliding slots; wherein, each of the ring sliders is provided with a gap, such that one end of the each of the two lock nuts passes through a respective one of the ring sliders.

2. The customized posterior atlantoaxial reduction fixator according to claim 1, wherein, a first end and a second end of the anti-rotation joint portion are 2-3 mm longer than a first and a second end of the U-shaped groove, respectively.

3. The customized posterior atlantoaxial reduction fixator according to claim 1, wherein, each of the two second heads is provided with a long arm nail groove, with an annular recess configured on a middle part of an outer wall.

4. The customized posterior atlantoaxial reduction fixator according to claim 3, wherein, the each of the two second heads is separated into upper and lower portions through the annular recess, a ratio of a height of the upper portion to a height of the lower portion is N/1, wherein $N \geq 1$.

5. The customized posterior atlantoaxial reduction fixator according to claim 1, wherein, each of the two pulling-screws is a polyaxial screw, with the second head connected to the second body having a tapered thread tip.

6. The customized posterior atlantoaxial reduction fixator according to claim 1, wherein, the first body of each of the two supporting-screws is a single-axial screw fastened to the first head, having the tapered thread tip; or the first body of each of the two supporting-screws is a polyaxial screw fastened to the first head, having the tapered thread tip.

7. The customized posterior atlantoaxial reduction fixator according to claim 1, wherein, an external wall of the each of the two lock nuts comprises the head thread connected with one of the two first heads and a screw cap thread connected with one of the screw caps; a diameter of the head threads is greater than that of the screw cap threads, and is greater than that of the ring sliders; a diameter of the screw cap threads is less than that of the ring sliders, a diameter of an external wall of the screw cap is greater than that of the ring sliders; a through-hole with a hexagonal cross section is provided at a center of the each of the two lock nuts.

8. The customized posterior atlantoaxial reduction fixator according to claim 1, wherein, the bracing beam is a straight plate or a curved plate.

* * * * *